United States Patent
Clemmons

(10) Patent No.: US 6,245,023 B1
(45) Date of Patent: Jun. 12, 2001

(54) CONICAL BLOOD PRESSURE CUFF WITH RECTANGULAR BLADDER

(75) Inventor: John P. Clemmons, Tampa, FL (US)

(73) Assignee: Critikon Company, LLC, Tampa, FL (US)

( * ) Notice: Subject to any disclaimer, the term of this patent is extended or adjusted under 35 U.S.C. 154(b) by 0 days.

(21) Appl. No.: 09/378,005

(22) Filed: Aug. 19, 1999

(51) Int. Cl.⁷ ................................................. A61B 5/00
(52) U.S. Cl. ............................................ 600/499; 606/202
(58) Field of Search ..................................... 600/485, 490, 600/492–495, 497–499; 602/13; 606/202

(56) References Cited

U.S. PATENT DOCUMENTS

| | | |
|---|---|---|
| D. 411,011 * | 6/1999 | Schuster et al. ............. D24/165 |
| 3,633,567 | 1/1972 | Sarnoff . |
| 3,765,405 | 10/1973 | Natkanski . |
| 3,773,036 * | 11/1973 | Weyer ............................ 600/499 |
| 4,635,635 * | 1/1987 | Robinette-Lehman ........ 606/202 |
| 4,706,684 | 11/1987 | Sorensen . |
| 4,727,885 | 3/1988 | Ruff . |
| 4,832,040 | 5/1989 | Ruff . |
| 4,838,276 * | 6/1989 | Nagai et al. ................... 600/499 |
| 5,069,219 | 12/1991 | Knoblich . |
| 5,179,957 | 1/1993 | Williams . |
| 5,271,409 | 12/1993 | Millay . |
| 5,649,954 * | 7/1997 | McEwen ........................ 606/202 |
| 5,678,558 | 10/1997 | Johnson . |

* cited by examiner

Primary Examiner—Robert L. Nasser
(74) Attorney, Agent, or Firm—Laff, Whitesel & Saret, Ltd.

(57) ABSTRACT

A conical blood pressure cuff having an integrated inflatable bladder is provided. The cuff is formed of a flexible compliant laminate having at least first and second layers which are impermeable to air. The cuff is formed having first and second arcuate edges, the second edge having a smaller radius than the first edge. Radial edges extend between the first and second arcuate edges. An air-tight rectangular pocket forms the inflatable bladder between the first and second layers. A tube is provided communicating with the interior of the pocket formed between the laminated layers. Air may be pumped the through the tube to inflate the bladder. Similarly, the bladder may be deflated by removing air from the pocket through the tube.

20 Claims, 2 Drawing Sheets

CONICAL BLOOD PRESSURE CUFF WITH RECTANGULAR BLADDER

BACKGROUND OF THE INVENTION

The present invention relates to an improved inflatable cuff used for measuring a patient's blood pressure. Blood pressure results from the patient's heart pumping blood through the patient's body. As the heart periodically contracts, blood is forced through the arteries that extend throughout the body. With each contraction of the heart muscle, irregularly shaped pressure pulses propagate through the arteries, causing the arterial walls to flex or oscillate.

Two common methods used to measure a patient's blood pressure are the auscultatory method and the oscillometric method. In the auscultatory method, a cuff having an inflatable bladder associated therewith is secured around the patient's arm and the bladder is inflated. The inflated bladder, secured by the cuff, acts against the patient's arm to completely block the flow of blood through the brachial artery. The pressure in the cuff is then slowly reduced while a stethoscope is used to monitor the distal end of the artery to listen for pulsating sounds, known as Korotkoff sounds, that accompany the re-establishment of blood flow through the artery. The air pressure within the bladder is monitored as the pressure is reduced. The air pressure present in the bladder when Korotkoff sounds first appear is a measure of the systolic pressure, and the pressure in the bladder when the Korotkoff sounds disappear altogether (meaning that unrestricted blood flow has been reestablished) is a measure of the diastolic pressure.

The oscillometric method also employs a pressure cuff, however, rather than listening for the sound of the blood flowing through the artery, the oscillometric method measures blood pressure by measuring the flexing of the arterial wall. When the pressure cuff is inflated around the patient's arm, the flexing of the arteries adjacent the pressure cuff is transmitted to the inflated bladder. The flexing of the arteries causes minute, but detectable, pressure variations or pulses within the bladder which correspond to the flexing of the arteries. These pulses, also known as complexes, are affected by the pressure in the inflatable bladder. When the cuff pressure is approximately equal to the mean arterial pressure (MAP), the peak-to-peak amplitude of the complexes reaches a maximum value. Similarly, the peak-to-peak amplitude of the complexes is at a minimum when the cuff pressure is above the systolic pressure and below the diastolic pressure. Thus, by measuring these complexes at various cuff pressures, the mean arterial pressure and the diastolic and systolic pressures can be approximated.

It should be noted that the methods described above provide a non-invasive method for approximating the actual pressure of the blood flowing through the patient's arteries. The approximations employed in the methods described above are the result of an extensive body of research correlating blood pressure values measured using either the auscultatory or the oscillometric method against actual values obtained using more direct techniques. The majority of this research has been based on blood pressure cuffs having rectangular inflatable bladders. Furthermore, the shape of the bladder has a significant impact on blood pressure readings obtained using either the auscultatory or oscillometric method. Therefore, in order for blood pressure readings taken in the field to conform to the empirical research data, a rectangular inflatable bladder is highly desirable.

A significant number of patients who require regular blood pressure measurements are those suffering from hypertension. Many of these patients also suffer from clinical obesity. Obese patients often have upper arms that are not only large, but also have a characteristic conical shape. This conical shape is also exhibited in some patients having highly developed upper arm musculature.

Common rectangular blood pressure cuffs do not work effectively on patients having upper arms with a pronounced conical shape. When a rectangular cuff is wrapped conformally around the patient's upper arm, the ends of the cuff will overlap in an angular manner to conform to larger diameter of the patient's arm near the shoulder, and the smaller diameter of the arm near the elbow. Inflation of the bladder will cause a twisting movement of the overlapping closure, possibly pinching the patient's skin. If however, the cuff is wrapped as a cylinder conforming to the larger circumference of the patient's arm, a large air gap is formed between the cuff and the smaller circumference of the patient's upper arm at the opposite end. When the bladder is filled with air, a much larger volume of air is required to fill the lower portion of the bladder than is necessary to fill the upper portion. This too can lead to patient discomfort and, more importantly, inaccurate blood pressure readings. A further disadvantage to wrapping the blood pressure cuff in this manner is that the cuff tends to slide down the patient's arm due to the minimal surface area of skin contacting the cuff.

To resolve this problem, conical blood pressure cuffs have been developed. Existing conical cuffs include a separate bladder element which is inserted into a pocket located within the cuff. Both rectangular and conical bladder elements have been employed. However, conical bladders do not conform to the immense body of research that has been conducted based on rectangular bladder elements. Furthermore, the final dimensions of the bladder are defined by the size of the cuff pocket which constrains the bladder when the bladder is inserted and inflated therein. For conical cuffs with separate bladder elements, even rectangular bladder elements, the pocket tends to distort the natural inflated shape of the bladder, resulting in a deformed bladder shape that does not conform with the dimensional test data for rectangular bladders. What is more, the two component design is cumbersome to use and can lead to inaccurate readings.

Therefore, a need exists for a fully integrated conical blood pressure cuff wherein the inflatable bladder is formed directly with the cuff. Furthermore, in order for the readings obtained by such an integrated conical blood pressure cuff to conform to the large body of research data regarding blood pressure measurement, it is desirable that the integrated bladder have and retain a rectangular shape, even when conformally applied to a patient's conically shaped upper arm and inflated therearound.

SUMMARY OF THE INVENTION

The present invention provides a conical blood pressure cuff having an integrated rectangular inflatable bladder. The conical blood pressure cuff may be wrapped around the conical portion of a patient's upper arm in a straight manner without distorting the shape of the bladder, and without binding the patient's skin as the bladder is inflated.

The integrated blood pressure cuff and inflatable bladder is formed of a flexible, compliant laminate having at least two layers of material, both of which are impermeable to air. The laminate forms an arcuate substrate having first and second arcuate edges, with the second edge having a smaller radius than the first edge. Third and fourth radial edges extend between the first and second edges.

An air-tight rectangular pocket, or bladder, is formed between the first and second laminate layers. An inflating tube communicates with the interior of the pocket so that air may be pumped into and released from the pocket during the course of blood pressure examinations. A second inflating/ deflating tube may also be provided. Finally, a fastener is provided to secure the integrated blood pressure cuff around a patient's limb.

DETAILED DESCRIPTION OF THE PREFERRED EMBODIMENT

Figure 1:
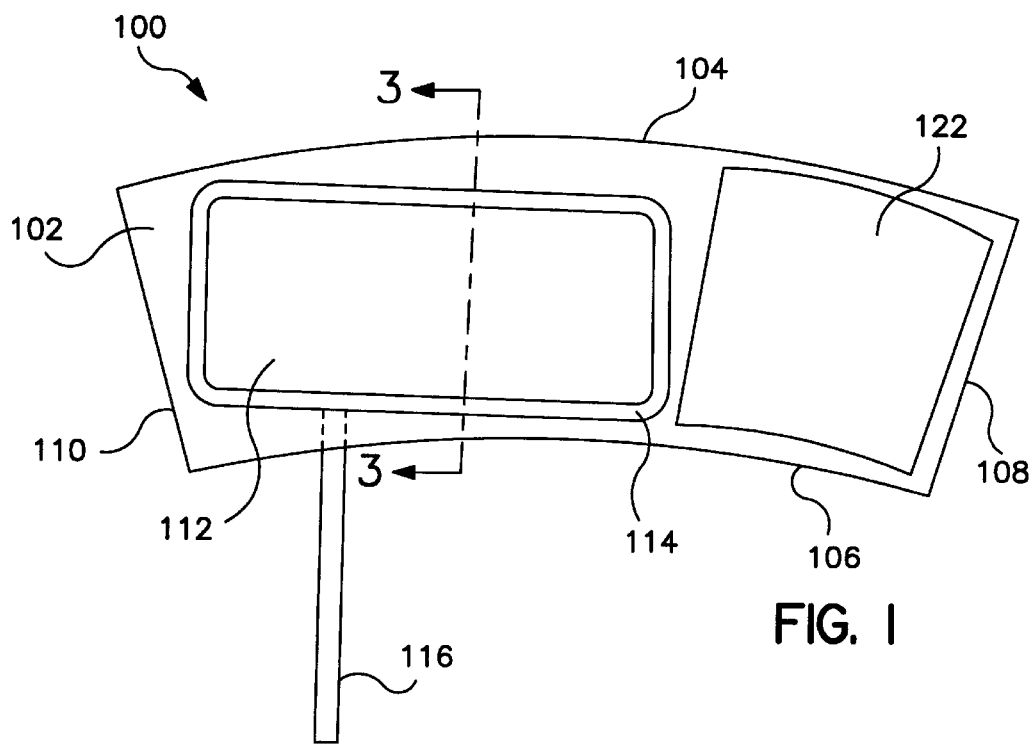
FIG. 1 is a plan view of an integrated conical blood pressure cuff according to the preferred embodiment of the invention.
Figure 2:
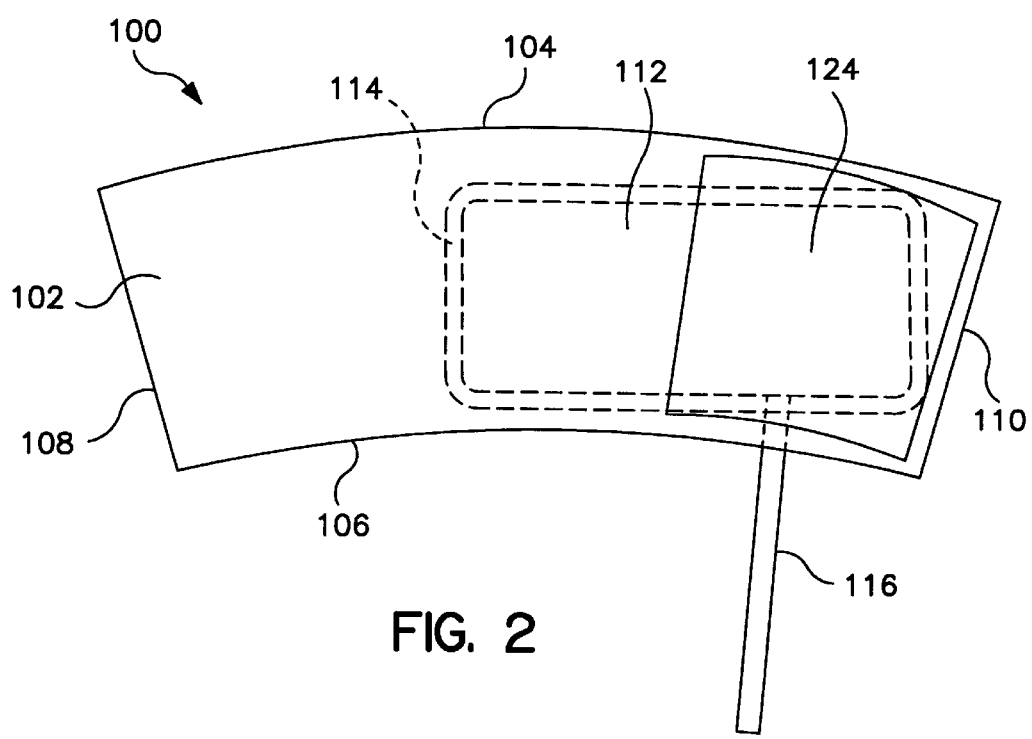
FIG. 2 is a plan view of the integrated conical blood pressure cuff of FIG. 1, showing the opposite side of the cuff from that shown in FIG. 1.
Figure 3:
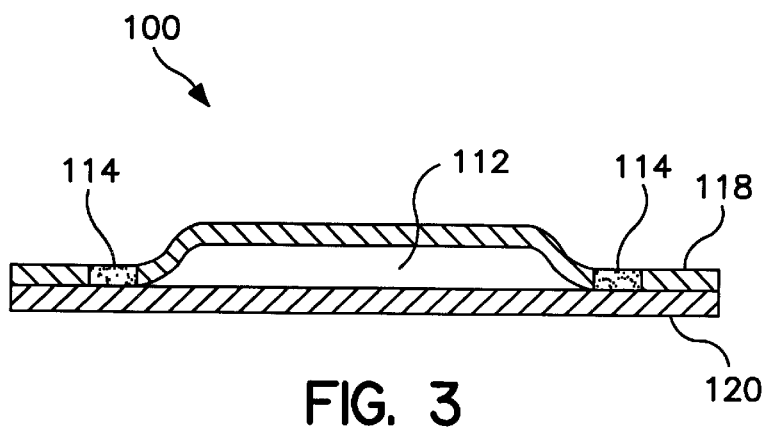
FIG. 3 is a cross section of the integrated conical blood pressure cuff of FIG. 1 taken along the line 3—3.

Referring to FIGS. 1, 2, and 3, a conical blood pressure cuff having an integrated rectangular inflatable bladder is shown at 100. The blood pressure cuff is formed of multi-layered substrate 102 comprising at least two layers 118, 120, each formed of a material impermeable air. Examples of suitable materials include a polymer film bonded to a cloth fabric by an adhesive, or a molten plastic extruded onto a cloth fabric. A cloth fabric is preferred for the inner layer of the cuff to provide a more comfortable surface for contacting the patient's skin, though other materials that are impermeable to air may also be employed. The substrate 102 is comprised of two layers that form an inflatable pocket therebetween. The layers are permanently and sealably bonded to one another around the edges of the pocket such that air introduced into the pocket cannot escape through the seams surrounding the pocket.

Substrate 102 is formed having an arcuate shape, with a larger radius outer edge 104, and a somewhat smaller radius inner edge 106. Radial side edges 108, 110 extend between the inner and outer edges 104, 106. A rectangular pocket 112, shown in cross section in FIG. 3, is formed between the layers of substrate 102. As noted above, in the preferred embodiment of the invention the inner layer 118 of substrate 102 comprises an impermeable cloth fabric and the outer layer 120 comprises a flexible compliant polymer film. Seams 114 are formed around the outer perimeter of the pocket so that the pocket retains it characteristic rectangular shape when air is introduced into pocket 112 to inflate the cuff. Seams 114 may be formed by stitching, or welding or any other suitable means for securely bonding and sealing the inner layer 118 to the outer layer 120 around the perimeter of the rectangular pocket 112. An inflating tube 116 extends between the layers of substrate 102, and communicates with the interior of pocket 112. Tube 116 allows air to be pumped into, and released from pocket 112. Alternate designs may include a second tube wherein air is pumped into the pocket through the first tube, and released through the second.

Figure 4:
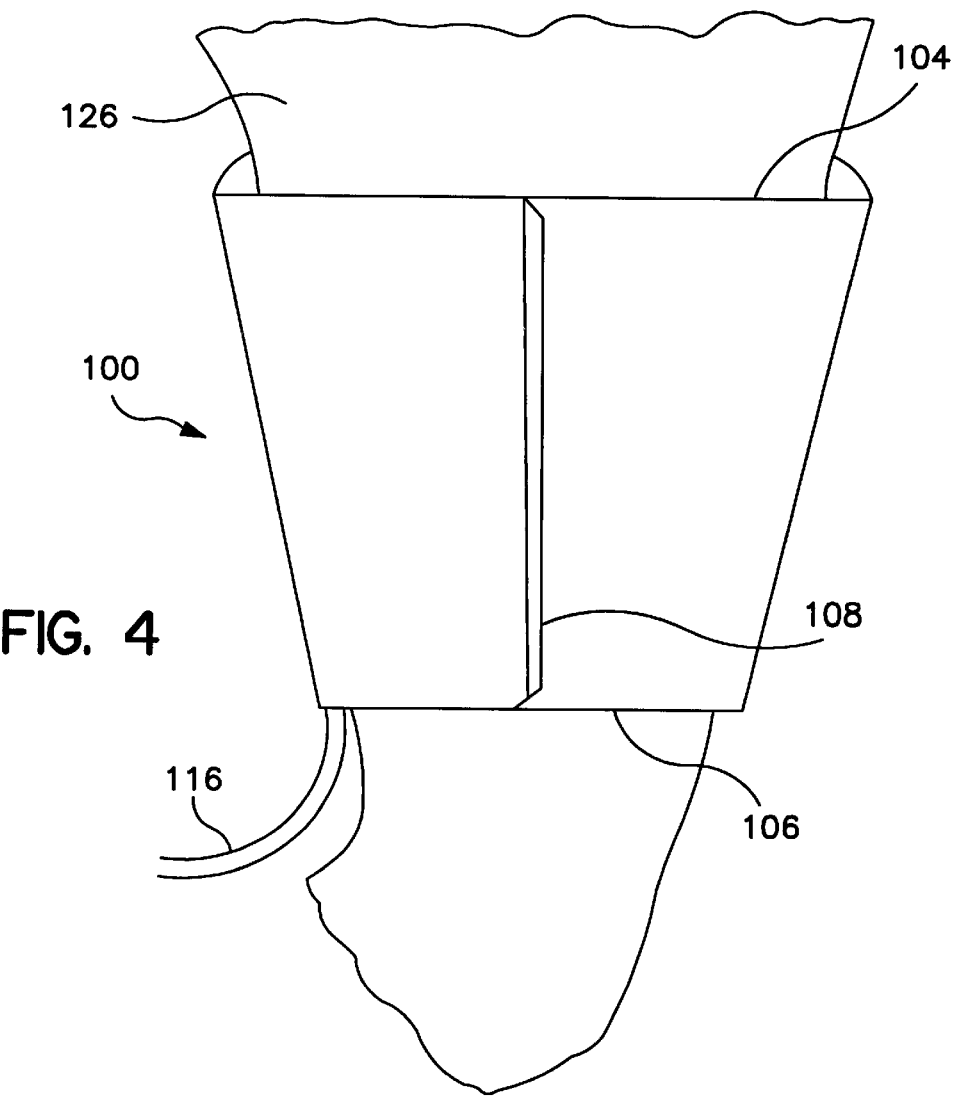
FIG. 4 is a plan view of the blood pressure cuff of claim 1 in use around a patient's arm.

A fastener is provided for securing the blood pressure cuff in a wrapped position around a patient's arm. In the preferred embodiment, a hook and loop adhesive type fastener is employed, wherein an adhesive patch 122 of polymer hooks is secured to the inner surface of substrate 102 near a first radial edge 108, and a second adhesive patch 124 comprising a plurality of loops is secured to the outer surface of the substrate near the opposite radial edge 110. Thus, when the blood pressure cuff is wrapped around a patient's arm, as shown in FIG. 4, the adhesive patches confront one another and may be securely joined. Alternately, the cuff may be self applied, employing a cinch ring or D-connector or an adhesive patch at one end to anchor one end of the cuff on the limb while the other end is wrapped around the limb and made fast.

As can be seen in FIG. 4, when the integrated blood pressure cuff is wrapped around the patient's arm 126, the larger diameter outer edge 104 forms a larger diameter ring conforming to the larger portion of the patient's upper arm. The smaller diameter inner edge 106 forms a smaller diameter ring conforming to the narrower portion of the patient's upper arm. Thus, the blood pressure cuff assumes a conical orientation, with the radial edges 108, 110 aligned relatively straight with one another. However, when air is pumped into pocket 112 to inflate the cuff, the pocket, or bladder, retains its characteristic rectangular shape. As the bladder inflates, there is no binding about the radial edges 108, 110 since the conical shape of the cuff allows the cuff to be wrapped in a straight manner around the patient's arm. Because the pocket 112, or inflatable bladder retains its shape rectangular shape, blood pressure measurements taken with the conical cuff may be relied upon as conforming with the standard body of knowledge accumulated with regard to standard rectangular cuffs.

It should be noted that various changes and modifications to the present invention may be made by those of ordinary skill in the art without departing from the spirit and scope of the present invention which is set out in more particular detail in the appended claims. Furthermore, those of ordinary skill in the art will appreciate that the foregoing description is by way of example only, and is not intended to be limiting of the invention as described in such appended claims.

What is claimed is:

1. A blood pressure cuff comprising:
    a flexible compliant laminate having at least first and second layers which are impermeable to air, said laminate having first and second arcuate edges, the second edge having a smaller radius than the first edge;
    an inflatable rectangular pocket formed between said first and second layers;
    a fastener to secure said laminate about a patient's limb when wrapped therearound.

2. The blood pressure cuff of claim 1 wherein the laminate comprises a polymer film bound by an adhesive to a cloth fabric.

3. The blood pressure cuff of claim 1 wherein the laminate comprises a moltent plastic extruded onto a cloth fabric.

4. The blood pressure cuff of claim 1 further comprising an air tight seam formed between said first and second layers surrounding the perimeter of said pocket.

5. The blood pressure cuff of claim 4 wherein said air tight seam is formed by stitching said second layer to said first layer.

6. The blood pressure cuff of claim 4 wherein said air tight seam is formed by welding said second later to said first layer.

7. The blood pressure cuff of claim 1 further comprising a tube communicating with an interior of said pocket whereby air may be introduced into and removed from said pocket.

8. The blood pressure cuff of claim 7 further comprising a second tube communicating with the interior of said pocket whereby said pocket is inflated by air introduced through said first tube, and deflated by air removed through said second tube.

9. An inflatable cuff for measuring blood pressure comprising a flexible arcuate substrate having a rectangular inflatable bladder integrally formed therewith, said arcuate substrate adapted to form a conical ring when secured around a patient's limb, with said bladder retaining its rectangular shape.

10. The inflatable cuff of claim 9 wherein said substrate comprises a laminate having at least two layers that are impermeable to air, and said inflatable bladder is formed in a pocket between said impermeable layers.

11. The inflatable cuff of claim 10 wherein the laminate comprises a polymer film bound by an adhesive to a cloth fabric.

12. The blood pressure cuff of claim 11 further comprising an air tight seam formed between said first and second layers surrounding the perimeter of said pocket.

13. The blood pressure cuff of claim 12 wherein said air tight seam is formed by stitching said second layer to said first layer.

14. The blood pressure cuff of claim 12 wherein said air tight seam is formed by welding said second later to said first layer.

15. The blood pressure cuff of claim 10 wherein the laminate comprises a moltent plastic extruded onto a cloth fabric.

16. The blood pressure cuff of claim 15 further comprising an air tight seam formed between said first and second layers surrounding the perimeter of said pocket.

17. The blood pressure cuff of claim 16 wherein said air tight seam is formed by stitching said second layer to said first layer.

18. The blood pressure cuff of claim 16 wherein said air tight seam is formed by welding said second later to said first layer.

19. The inflatable cuff of claim 9 further comprising a first tube communicating with an interior of said bladder whereby air may be introduced into said bladder.

20. The inflatable cuff of claim 19 further comprising a second tube communicating with the interior of said bladder whereby air is removed from said bladder.

* * * * *